(12) United States Patent
Lee et al.

(10) Patent No.: US 10,092,233 B2
(45) Date of Patent: Oct. 9, 2018

(54) METHOD AND APPARATUS FOR NON-INVASIVE LIVER FUNCTION TESTING

(71) Applicant: SAMSUNG ELECTRONICS CO., LTD., Suwon-si (KR)

(72) Inventors: Joonhyung Lee, Yongin-si (KR); Sangkyu Kim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 683 days.

(21) Appl. No.: 14/695,461

(22) Filed: Apr. 24, 2015

(65) Prior Publication Data

US 2016/0045151 A1 Feb. 18, 2016

(30) Foreign Application Priority Data

Aug. 12, 2014 (KR) ........................ 10-2014-0104533

(51) Int. Cl.
*A61B 5/00* (2006.01)
*A61B 5/145* (2006.01)
*A61B 5/1455* (2006.01)

(52) U.S. Cl.
CPC ............ *A61B 5/4244* (2013.01); *A61B 5/004* (2013.01); *A61B 5/0075* (2013.01); *A61B 5/1455* (2013.01); *A61B 5/14546* (2013.01); *A61B 2562/0233* (2013.01); *A61B 2576/02* (2013.01)

(58) Field of Classification Search
CPC ........ A61B 2562/0233; A61B 2576/02; A61B 5/004; A61B 5/0075; A61B 5/14546; A61B 5/1455; A61B 5/4244
See application file for complete search history.

(56) References Cited

U.S. PATENT DOCUMENTS

| 6,565,738 B1 | 5/2003 | Henning et al. |
| 9,597,021 B1* | 3/2017 | Gupta .................. A61B 5/1455 |
| 2014/0073043 A1* | 3/2014 | Holmes .................. G01N 35/00 |
| | | 435/287.3 |

FOREIGN PATENT DOCUMENTS

| KR | 1020040063358 A | 7/2004 |
| KR | 100729147 B1 | 6/2007 |
| KR | 1020070117993 A | 12/2007 |

(Continued)

OTHER PUBLICATIONS

Huang et al. "Aspartate Aminotransferase (AST/GOT) and Alanine Aminotransferase (ALT/GPT) Detection Techniques", Sensors 2006, 6, 756-782.*

(Continued)

*Primary Examiner* — Michael Rozanski
(74) *Attorney, Agent, or Firm* — Sughrue Mion, PLLC

(57) ABSTRACT

Disclosed are a non-invasive liver function testing apparatus and method. The non-invasive liver function testing apparatus includes a light source configured to irradiate light onto an object, a light detector configured to detect information about light reflected from the object, a raw data extractor configured to extract raw data, associated with at least one target material constituting the object, from the information detected by the light detector, and a data processor configured to extract liver function-related information, including a correlation with the at least one target material, from the raw data.

20 Claims, 14 Drawing Sheets

(56) References Cited

FOREIGN PATENT DOCUMENTS

WO 2008078319 A1 7/2008

OTHER PUBLICATIONS

Pleitez et al., "In Vivo Noninvasive Monitoring of Glucose Concentration in Human Epidermis by Mid-Infrared Pulsed Photoacoustic Spectroscopy", Analytical Chemistry 2013, 85, pp. 1013-1020.

\* cited by examiner

METHOD AND APPARATUS FOR NON-INVASIVE LIVER FUNCTION TESTING

RELATED APPLICATION

This application claims priority from Korean Patent Application No. 10-2014-0104533, filed on Aug. 12, 2014, in the Korean Intellectual Property Office, the disclosure of which is incorporated herein in its entirety by reference.

BACKGROUND

1. Field

The present disclosure relates to methods and apparatuses for testing liver function in a non-invasive manner.

2. Description of the Related Art

With advancements in medicine, the average life span of people is gradually increasing. The reasons for this include advances in medicine, increased interest of people in health, and enhanced health management.

Since a number of medical apparatuses for checking health have been developed, people may directly check their health without having to go to hospital. Examples of adult diseases include cerebrovascular disease, hypertension, diabetes, liver disease, etc. For example, diabetic patients may frequently check their blood sugar levels with a small blood sugar tester without having to go to hospital. Since blood pressure apparatuses are provided at many places such as public institutions, people may frequently check their blood pressure. In Korea, liver disease occurs in many people, and thus, a liver somatic index is measured by collecting blood so as to check for liver disease. However, blood collection inflicts pain and a psychological burden on people. Also, frequent blood collection may be harmful, and for this reason, it is difficult to frequently test liver function.

SUMMARY

Provided are apparatuses for testing liver function in a non-invasive manner.

Provided are methods of testing liver function in a non-invasive manner.

Additional aspects will be set forth in part in the description which follows and, in part, will be apparent from the description, or may be learned by practice of the presented embodiments.

According to an aspect of an example embodiment, a non-invasive liver function testing apparatus includes: a light source configured to irradiate light onto an object; a light detector configured to detect information about light reflected from the object; a raw data extractor configured to extract raw data, associated with at least one target material constituting the object, from the information detected by the light detector; and a data processor configured to draw liver function-related information, including a correlation with the at least one target material, from the raw data.

The light detector may include a spectrometer configured to divide the light reflected from the object to generate a spectrum.

The raw data extractor may include a spectrum analyzer configured to extract the raw data, associated with the at least one target material constituting the object, from the spectrum.

The spectrometer may include an infrared spectrometer.

The spectrometer may include a mid-infrared spectrometer or a near-infrared spectrometer.

The spectrometer may include a FT-IR spectrometer.

The spectrometer may include a Raman spectrometer.

The spectrometer may further include an attenuated total reflectance prism.

The data processor may include information about a correlation between the raw data of the at least one target material and the liver function-related information.

The information about the correlation may include a correlational formula or a lookup table.

The at least one target material may include at least one functional group selected from the group consisting of a —COOH group, a —C=O group, and a —C—N group.

The liver function-related information may include a concentration of at least one enzyme selected from the group consisting of aspartate transaminase (AST), liver transminase (ALT), and γ-gamma glutamyl transpeptidase (GTP).

The raw data may include data of light intensity with respect to a wavenumber corresponding to the at least one target material in a spectrum which is acquired by the light reflected from the object.

The wavenumber may include at least one selected from the group consisting of 1,740 cm-1, 1,670 cm-1 to 1,820 cm-1, and 1,080 cm-1 to 1,360 cm-1.

The at least one target material may include a material that is positioned at a first depth of the object, the liver function-related information may include information of a material that is positioned at a second depth of the object, and the first depth may be less than the second depth.

According to another aspect of an example embodiment, a non-invasive liver function testing method includes: irradiating light onto an object; detecting, by a light detector, information about light reflected from the object; extracting raw data, associated with at least one target material constituting the object, from the information detected by the light detector; and drawing liver function-related information, including a correlation with the at least one target material, from the raw data.

The detecting of the information may include dividing the light reflected from the object by a spectrometer to generate a spectrum.

The extracting of the raw data may include extracting the raw data, associated with the at least one target material constituting the object, from the spectrum.

The detecting of the information may be performed by an infrared spectrometer.

The non-invasive liver function testing method may further include: directly measuring the liver function-related information from a plurality of objects; collecting data which is output by a reaction between the at least one target material and the light; and acquiring a correlation between the liver function-related information and the data.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
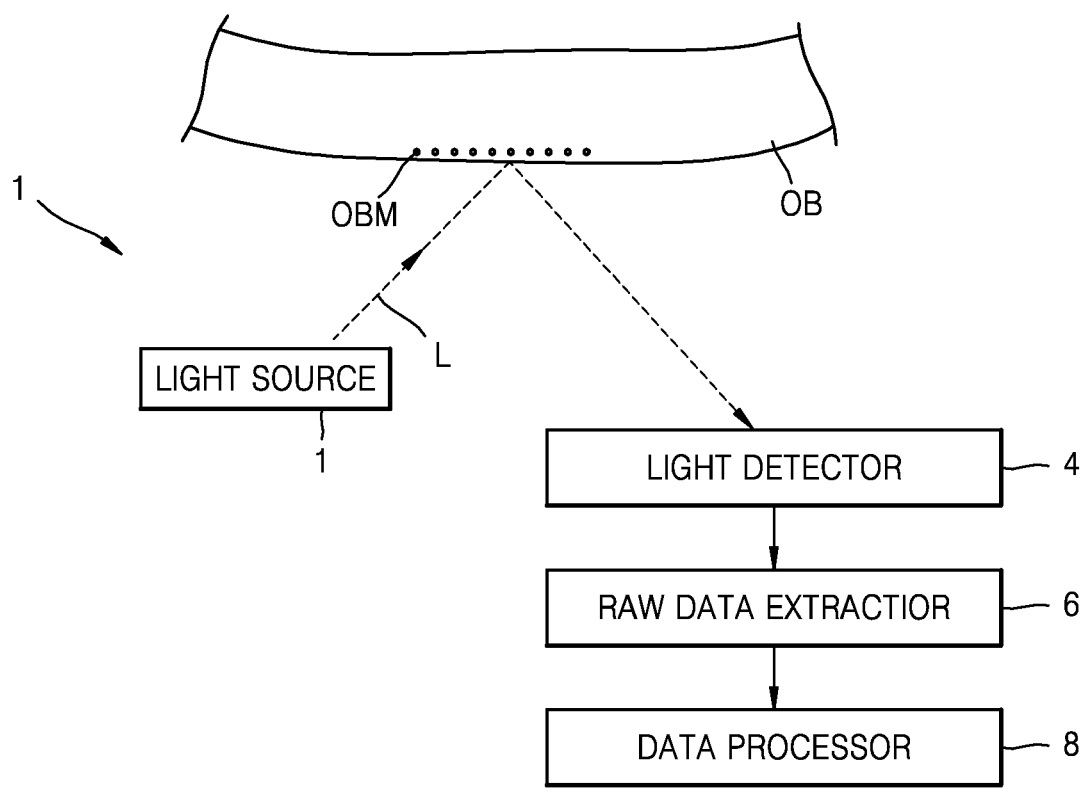
FIG. 1 schematically illustrates a non-invasive liver function testing apparatus according to an exemplary embodiment.

Reference will now be made in detail to exemplary embodiments, examples of which are illustrated in the accompanying drawings, wherein like reference numerals refer to like elements throughout. In this regard, the exemplary embodiments may have different forms and should not be construed as being limited to the descriptions set forth herein. Accordingly, the exemplary embodiments are merely described below, by referring to the figures, to explain aspects of the present description.

Hereinafter, a non-invasive liver function testing apparatus and method according to exemplary embodiments will be described in detail with reference to the accompanying drawings.

In the drawings, like reference numerals refer to like elements, and the size and thickness of each element may be exaggerated for clarity and convenience of description. Embodiments to be described below are merely exemplary, and the exemplary embodiments may be variously modified. For example, when it is described that a layer is provided on, over, or above a substrate or another layer, the layer may be disposed on the other layer in direct contact with the other layer, and another layer may be formed therebetween.

FIG. 1 schematically illustrates a non-invasive liver function testing apparatus 1 according to an exemplary embodiment.

The non-invasive liver function testing apparatus 1 includes a light source 1 configured to irradiate light L onto an object OB, a light detector 4 configured to detect information about light reflected from the object OB, and a raw data extractor 6 configured to extract raw data, which is associated with at least one target material OBM constituting the object OB, from the information detected by the light detector 4.

The object OB is a target object to be tested, and may be a body, for example, a person or an animal. The light source 1 may irradiate visible light or infrared light, or may be a laser that irradiates light of a short wavelength. However, the light source 1 is not limited thereto, and may be variously selected depending on a characteristic based on an interaction between light and the object OB.

The light detector 4 detects light reflected from the object OB, and may use various methods. The raw data extractor 6 may analyze light detected from the light detector 4 to extract raw data associated with the target material OBM of the object OB. The raw data may be, for example, data which reflects in an interaction between input light and the target material OBM. For example, the raw data may be acquired from a relationship between a wavelength or a wavenumber of light and an intensity of the light.

The non-invasive liver function testing apparatus 1 may include a data processor 8 configured to process the raw data. The data processor 8 may draw liver function-related information, including a correlation with the at least one target material OBM, from the raw data. The liver function-related information may include information about an enzyme of a liver, information about a synthesis function of the liver, and information about a detoxification function of the liver. For example, the information about the enzyme of the liver may include, for example, a concentration of at least one enzyme selected from the group consisting of γ-gamma glutamyl transpeptidase (GTP), aspartate transaminase (AST), and liver transminase (ALT).

γ-GTP is an enzyme that is in biliary ducts in a liver, and may increase when excretion of bile is abnormal. γ-GTP may be relevant to a glutathione metabolism reaction in a tissue of an object. For example, γ-GTP may act as a catalyst in the following reaction in the tissue of the object.

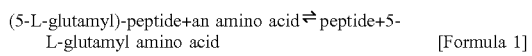
(5-L-glutamyl)-peptide+an amino acid ⇌ peptide+5-L-glutamyl amino acid     [Formula 1]

Figure 2:
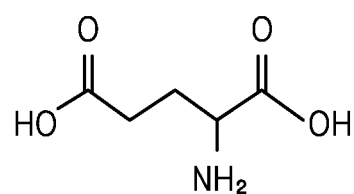
FIGS. 2 to 4 illustrate a reaction chemical formula of a liver function enzyme.

According to the reaction formula, in a tissue, the more glutamyl moiety, the more γ-GTP. When a left material of Formula 1 is reduced, or a right material of Formula 1 increases, there may be more γ-GTP. Alternatively, one selected from a reduction speed of the left material of Formula 1 and an increase speed of the right material of Formula 1 is measured, and a relationship between the measured value and a concentration of γ-GTP may be obtained. A spectrum is continuously measured, and the reduction speed of the left material of Formula 1 and the increase speed of the right material of Formula 1 are extracted from a change in the measured spectrum. For example, the concentration of γ-GTP may be indirectly measured by quantifying glutamate of a tissue by using a non-invasive method. In other words, a light characteristic of glutamate is obtained by using a light-based non-invasive method, and information about γ-GTP is drawn from the light characteristic of glutamate. FIG. 2 illustrates a molecular structure of glutamate.

A concentration of AST may increase when a liver cell is damaged by an enzyme of a liver cell and an enzyme of a heart cell. AST may act as a catalyst in a tissue in the following reaction.

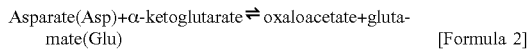
Asparate(Asp)+α-ketoglutarate ⇌ oxaloacetate+glutamate(Glu)     [Formula 2]

For example, in a reaction formula of Formula 2, when a left material is reduced, or a right material increases, there may be more AST. Alternatively, at least one selected from a reduction speed of the left material of Formula 2 and an increase speed of the right material of Formula 2 is measured, and a relationship between the measured value and a concentration of AST may be obtained.

Figure 3:
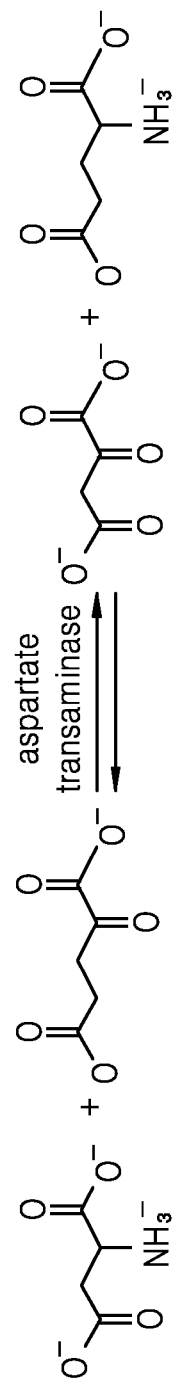

FIG. 3 illustrates a molecular structure based on the reaction formula of Formula 2. For example, a material having a correlation with AST may include at least one selected from the group consisting of aspartate, α-ketoglutarate, oxaloacetate, and glutamate. For example, the material having the correlation with AST may include at least one functional group selected from the group consisting of a —COOH (carboxylic acid) functional group, a —C=O (carbonyl) functional group, and a —C—N functional group. A normal liver somatic index range of AST may have, for example, a range of 0 IU/L to 40 IU/L.

ALT is an enzyme which is in a liver cell, and when the liver cell is damaged, a concentration of ALT increases. ALT may act as a catalyst in a tissue of an object in the following reaction.

  [Formula 3]

For example, in a reaction formula of Formula 3, when a left material is reduced, or a right material increases, there may be more ALT. Alternatively, at least one selected from a reduction speed of the left material of Formula 3 and an increase speed of the right material of Formula 3 is measured, and a relationship between the measured value and a concentration of ALT may be obtained.

Figure 4:
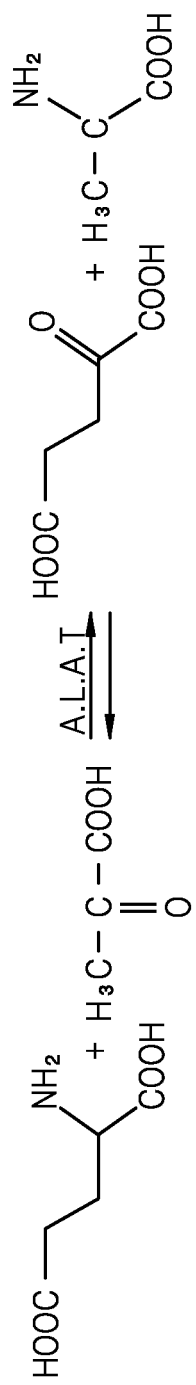

FIG. 4 illustrates a molecular structure based on the reaction formula of Formula 3. For example, a material having a correlation with ALT may include at least one selected from the group consisting of L-gluramate, pyruvate, α-ketoglutarate, and L-alanine. A normal liver somatic index range of ALT may have, for example, a range of 0 IU/L to 40 IU/L.

The raw data extractor 6 may include raw data associated with at least one target material constituting an object and an algorithm that calculates a correlation with liver function-related information. For example, the correlation may be expressed as a relational formula between the raw data associated with the at least one target material and the liver function-related information. The raw data extractor 6 may obtain the liver function-related information from the raw data, based on the algorithm. The liver function-related information may include, for example, a liver enzyme concentration.

The raw data associated with the at least one target material may include, for example, a light characteristic associated with the at least one target material. The raw data associated with the at least one target material may include, for example, light intensity with respect to a wavelength (or a wavenumber) associated with the at least one target material.

Figure 5:
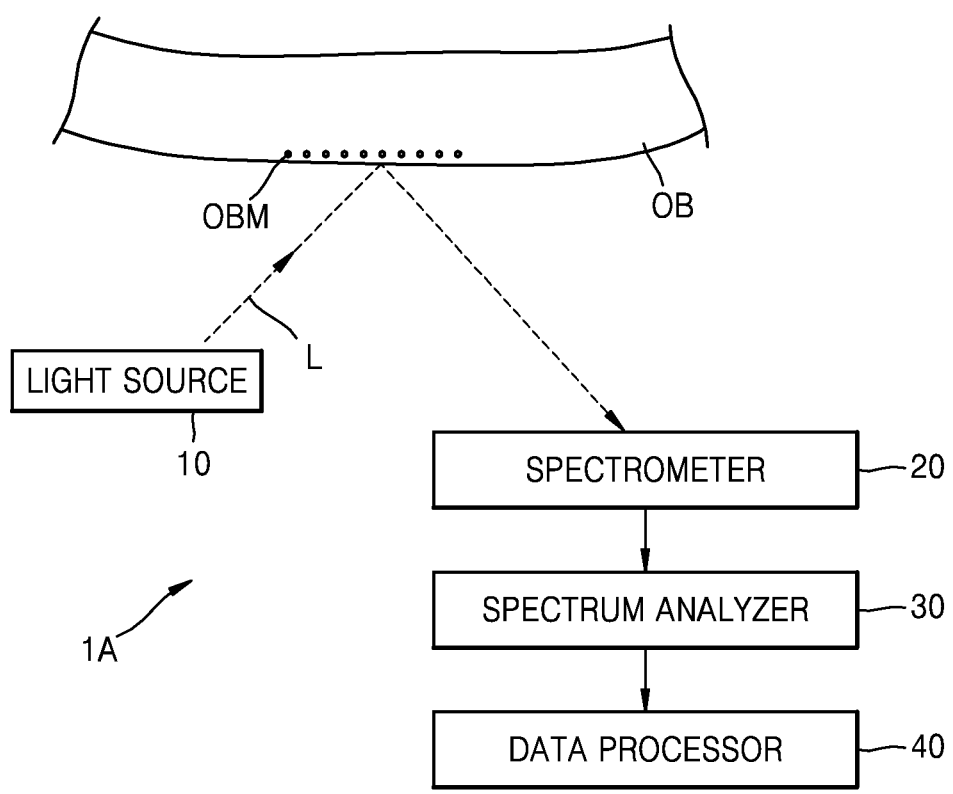
FIG. 5 schematically illustrates a non-invasive liver function testing apparatus according to an exemplary embodiment.

FIG. 5 illustrates an exemplary embodiment.

A non-invasive liver function testing apparatus 1A of FIG. 5 may include a light source 10 that irradiates light L onto an object OB, a spectrometer 20 that divides light reflected from the object OB to acquire a spectrum, a spectrum analyzer 30 that extracts raw data, which is associated with at least one target material OBM constituting the object OB, from the spectrum, and a data processor 40 that draws liver function-related information, including a correlation with the at least one target material OBM, from the raw data.

The light source 10 may irradiate, for example, infrared light. The infrared light may include, for example, mid-infrared light or near-infrared light. However, the light source 10 is not limited thereto, and may be variously selected depending on a characteristic based on an interaction between light and the object OB.

The spectrometer 20 may divide and detect light reflected from the object OB. The spectrometer 20 may be an example of a light detector. The spectrometer 20 may be, for example, an infrared spectrometer. The infrared spectrometer may acquire a spectrum which is obtained by dividing light reflected from an object. The spectrometer 20 may include a mid-infrared spectrometer or a near-infrared spectrometer. The mid-infrared spectrometer may have a spectrum having a range of 2.5 μm to 20 μm.

The spectrum analyzer 30 may extract the raw data, which is associated with the at least one target material OBM included in the object OB, from the spectrum acquired by the spectrometer 20. For example, the spectrum analyzer 30 may obtain a light characteristic (for example, light intensity (or an absorbance) with respect to a wavelength or a wavenumber) corresponding to the at least one target material OBM. The spectrum analyzer 30 may be an example of the raw data extractor 6. The spectrum analyzer 30 may analyze light detected by the light detector 4 to extract the raw data associated with the target material OBM of the object OB. The raw data may be, for example, data which reflects an interaction between input light and the target material OBM.

The data processor 40 may include raw data associated with at least one target material constituting an object and an algorithm that includes a correlation with liver function-related information. The data processor 40 may obtain the liver function-related information from the raw data, based on the algorithm. The liver function-related information may include, for example, a liver enzyme concentration. A liver enzyme and at least one target material having a correlation with the liver enzyme are as described above, and thus, their detailed descriptions will not be repeated here.

A non-invasive liver function testing apparatus may test a liver function in a non-invasive method without collecting blood. A liver enzyme concentration representing a liver somatic index may be directly obtained from blood, but in the present embodiment, the liver enzyme concentration may be indirectly obtained by the non-invasive method by using light. Therefore, since it is not required to directly collect blood, a liver function of an examinee is more conveniently tested, and a liver function test may be more simply and frequently tested. In an exemplary embodiment, raw data of a target material having a correlation with a liver function enzyme may be measured, and a liver function enzyme concentration may be drawn.

Figure 6:
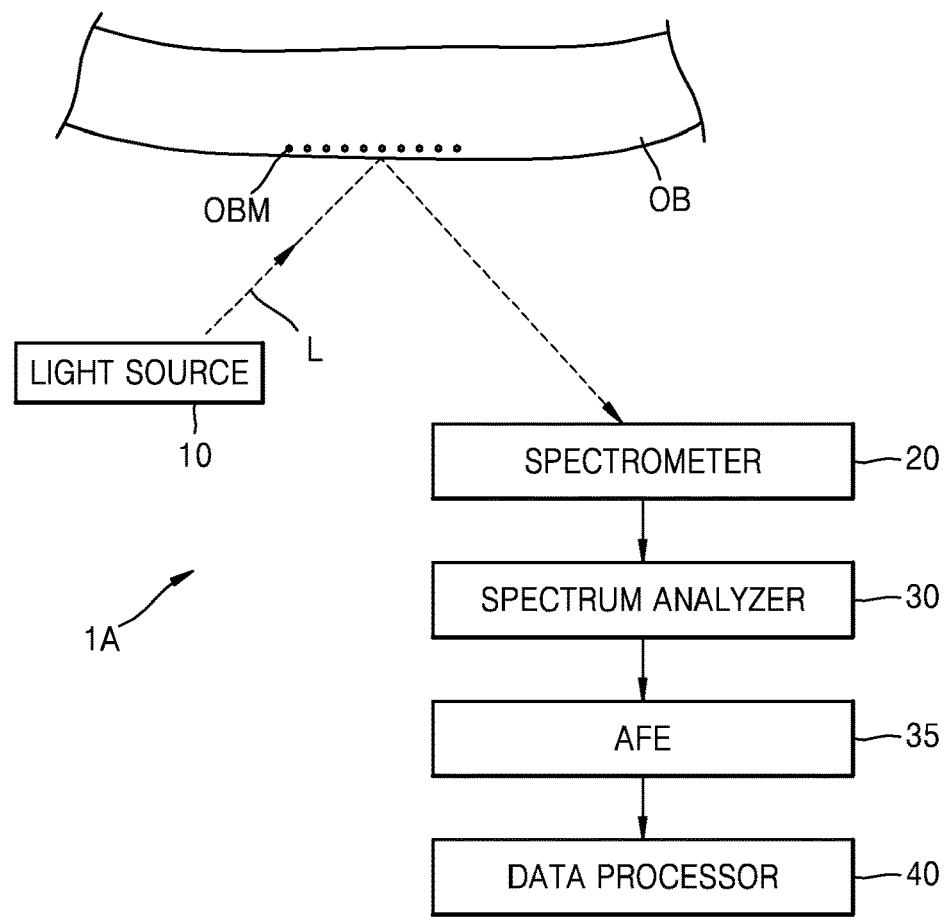
FIG. 6 illustrates an example in which the non-invasive liver function testing apparatus of FIG. 5 further includes an analog front end (AFE)

FIG. 6 illustrates an example in which an analog front end (AFE) 35 is further provided between the spectrum analyzer 30 and the data processor 30 in the non-invasive liver function testing apparatus of FIG. 5. The AFE 35 may convert an analog signal, obtained from the spectrum analyzer 30, into a digital signal.

For example, at least one target material may be located at a first depth of an object, and a liver function enzyme may be located at a second depth of the object. For example, the first depth may be less than the second depth. Alternatively, for example, the at least one target material may be in a tissue of the object, and the liver function enzyme may be in blood of the object.

Figure 7:
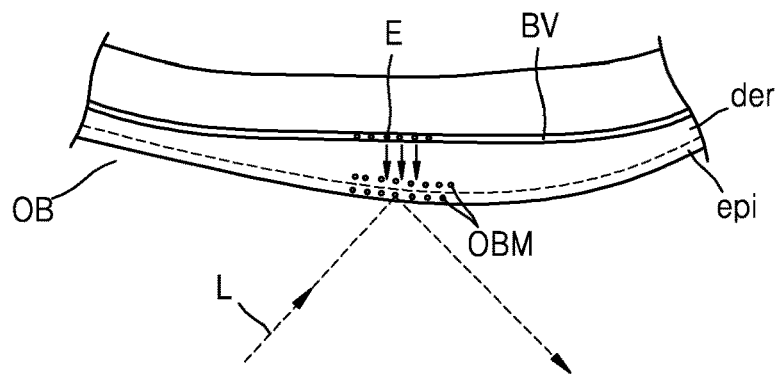
FIG. 7 illustrates that a non-invasive liver function testing apparatus according to an exemplary embodiment irradiates light onto an object.
Figure 8A:
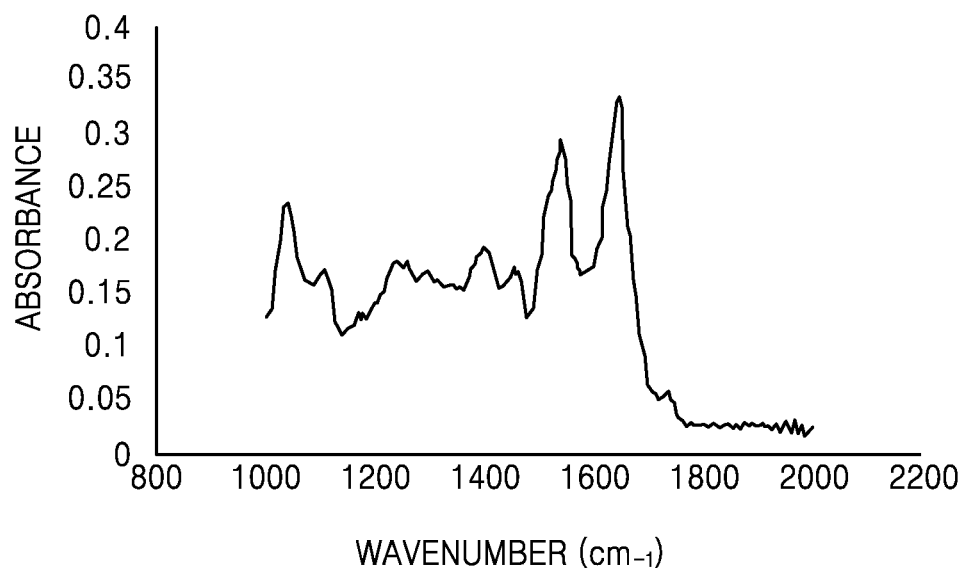
FIGS. 8A to 8H show absorption spectrums obtained from a non-invasive liver function testing apparatus according to an exemplary embodiment.
Figure 8B:
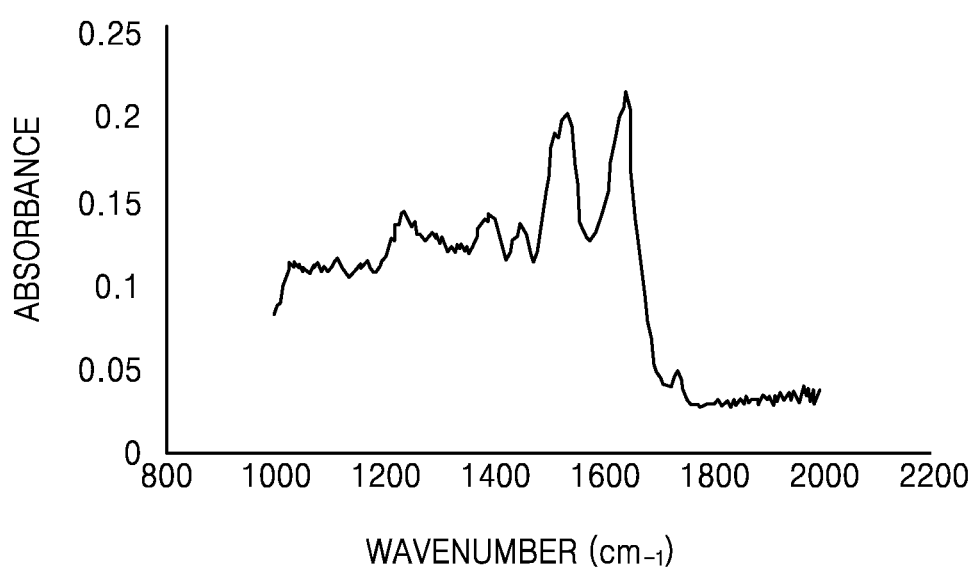
Figure 8C:
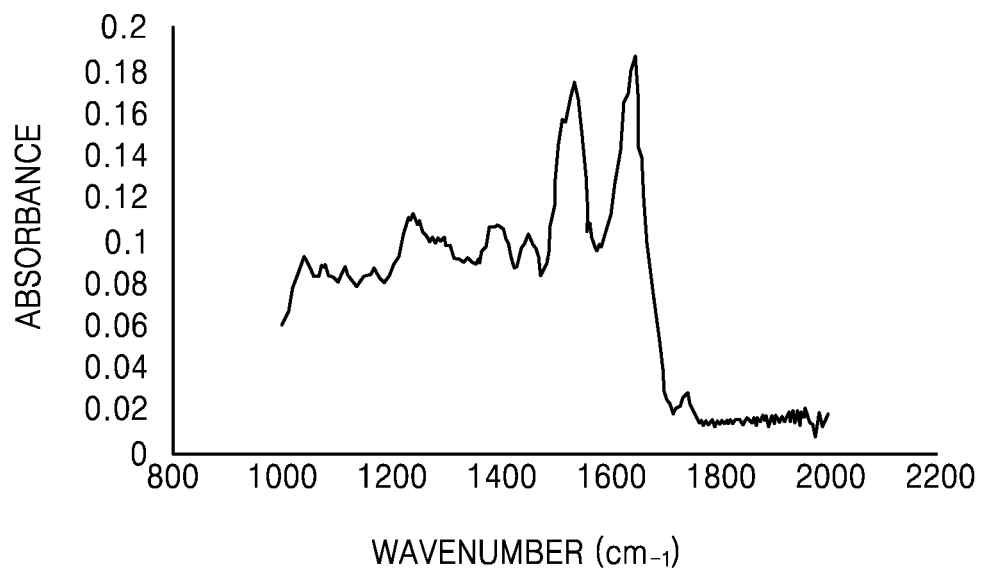
Figure 8D:
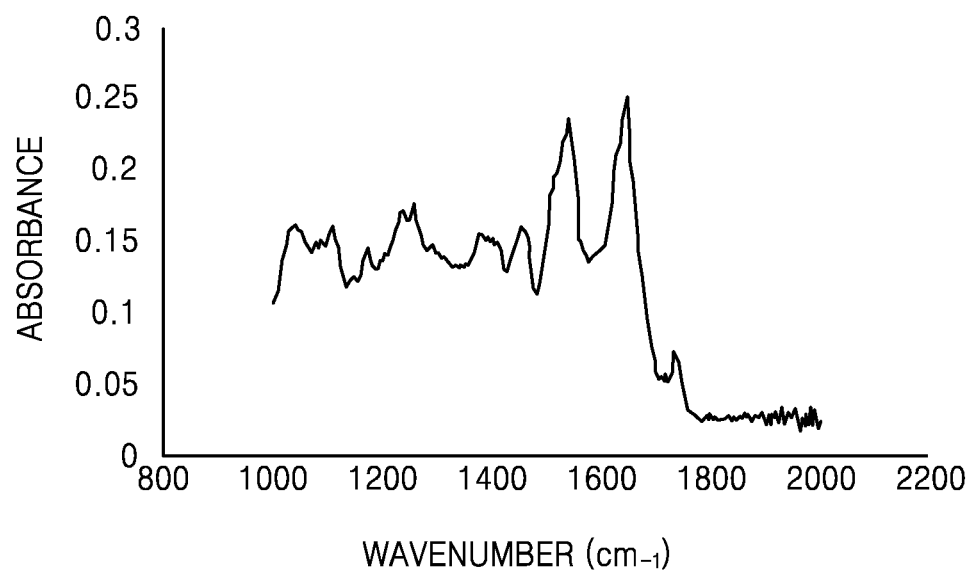
Figure 8E:
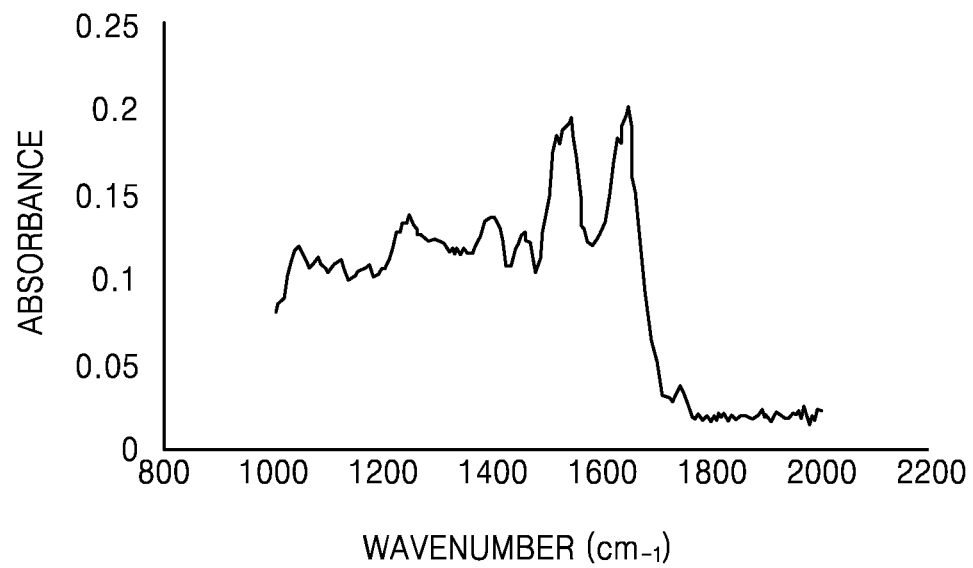
Figure 8F:
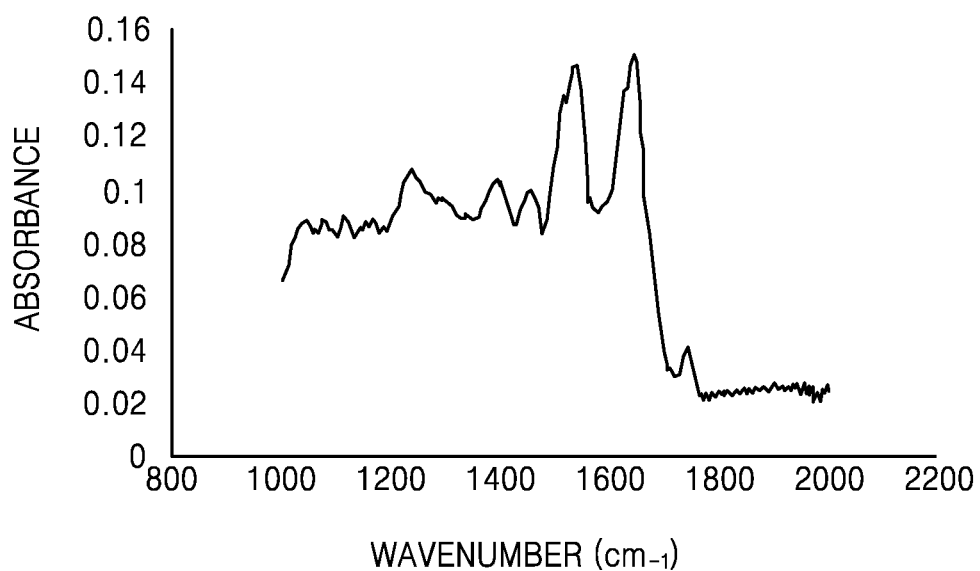
Figure 8G:
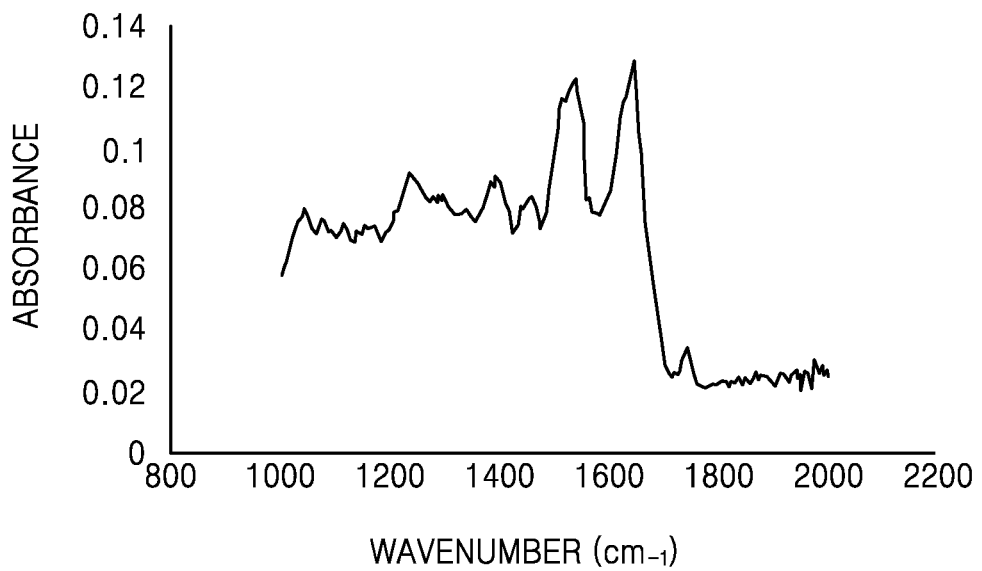
Figure 8H:
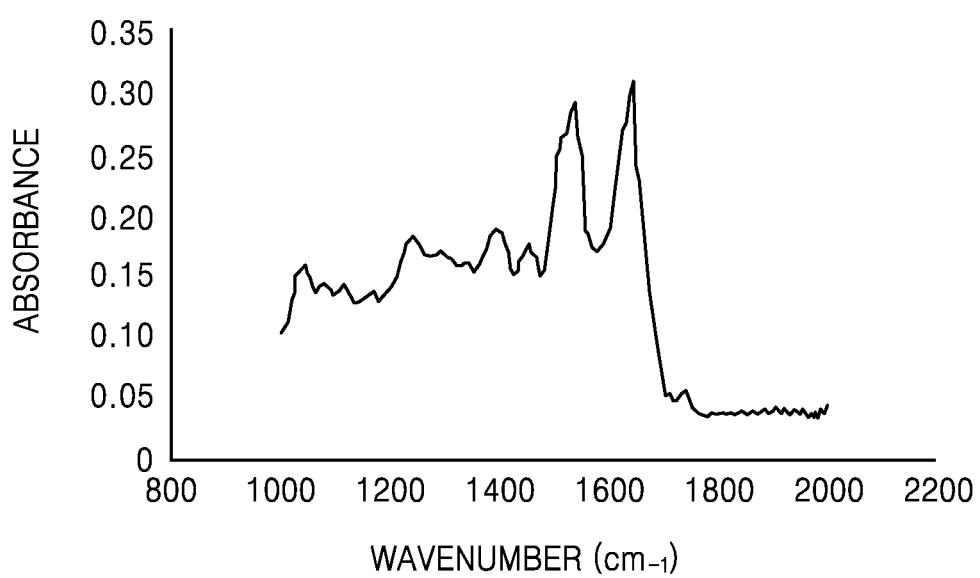

FIG. 7 schematically illustrates a skin and a blood vessel BV of an object OB. The skin may include epidermis (epi)

which is positioned at a surface and dermis (der) which is positioned under the epidermis. The blood vessel BV is positioned at a deeper position than the dermis (der). For example, the at least one target material may be positioned at the epidermis (epi) or the dermis (der), and a liver function enzyme E may be positioned in the blood vessel BV. Here, for example, it may be assumed that the liver function enzyme E in the blood vessel BV is diffused and moves out of the blood vessel BV, and thus, the at least one target material has a deformed shape. However, this is merely assumed, and the present embodiment is not limited thereto.

The light L from the light source 10 may be transmitted to the epidermis (epi) or the dermis (der). However, a transmission depth of light is not limited thereto, and may be changed depending on an intensity of light or force with which a test apparatus is pressed to an object.

FIGS. 8A to 8H are spectrums showing absorbance with respect to wavenumbers of lights reflected from a plurality of objects OB. An absorbance with respect to an absorption wavenumber (or an absorption wavelength) corresponding to a target material of interest may be acquired from an absorption spectrum. A wavenumber (or a wavelength) corresponding to a target material, for which an absorbance is to be obtained from the absorption spectrum, may use a priori data for each material. For example, a —COOH group may have an absorption wavenumber of 1,740 cm$^{-1}$. A —C=O group may have an absorption wavenumber having a range of 1,670 cm$^{-1}$ to 1,820 cm$^{-1}$. A —C—N group may have, for example, an absorption wavenumber having a range of 1,080 cm$^{-1}$ to 1,360 cm$^{-1}$. For example, an absorbance with respect to an absorption wavenumber of the —COOH group which is one of main molecular structures of glutamate may be acquired as raw data. Alternatively, raw data based on at least one functional group selected from the group consisting of —COOH group, —C=O group, and —C—N group may be acquired.

The data processor 40 may include raw data associated with at least one target material and information about a correlation with liver function-related information. The liver function-related information may be drawn from the raw data by using the correlation.

For example, the data processor 40 may include raw data associated with at least one target material and information and a correlational formula with liver function-related information. Alternatively, the data processor 40 may include a lookup table of the raw data associated with at least one target material and the liver function-related information corresponding to the raw data. The data processor 40 may include the raw data of the at least one target material, which is previously extracted by various methods, and information about a correlation with the liver function-related information.

For example, the correlation may be extracted by an algorithm which processes the raw data associated with the at least one target material and liver function-related data.

Next, an example of extracting a correlation between raw data of a target material and liver function-related information will be described.

A liver enzyme concentration is measured by collecting blood from a plurality of objects OB. For example, a γ-GTP concentration is measured by collecting blood from several people.

Data of a target material is collected from the plurality of objects OB. For example, light is irradiated onto the plurality of objects OB, and an absorption spectrum of each of the plurality of objects OB is obtained by using a spectrometer. As shown in FIGS. 8A to 8H, an absorption spectrum of light reflected from each object OB is obtained by using the spectrometer. An absorbance corresponding to an absorption wavenumber with respect to the target material may be acquired from each absorption spectrum. For example, the target material may include a —COOH group of glutamate, and an absorption wavenumber may be 1,740 cm$^{-1}$. This is only an example, and the target material may be variously changed.

Subsequently, a correlation between the measured γ-GTP concentration and the absorbance of the target material obtained from the absorption spectrum may be drawn. The correlation may be obtained by using various algorithms. Here, the correlation may be expressed as a formula. However, the correlation is not limited thereto, and may be implemented as a lookup table of a light characteristic (for example, an absorbance) of the target material and liver function-related information (for example, the γ-GTP concentration). In addition, the correlation may be implemented in various forms.

Figure 9:
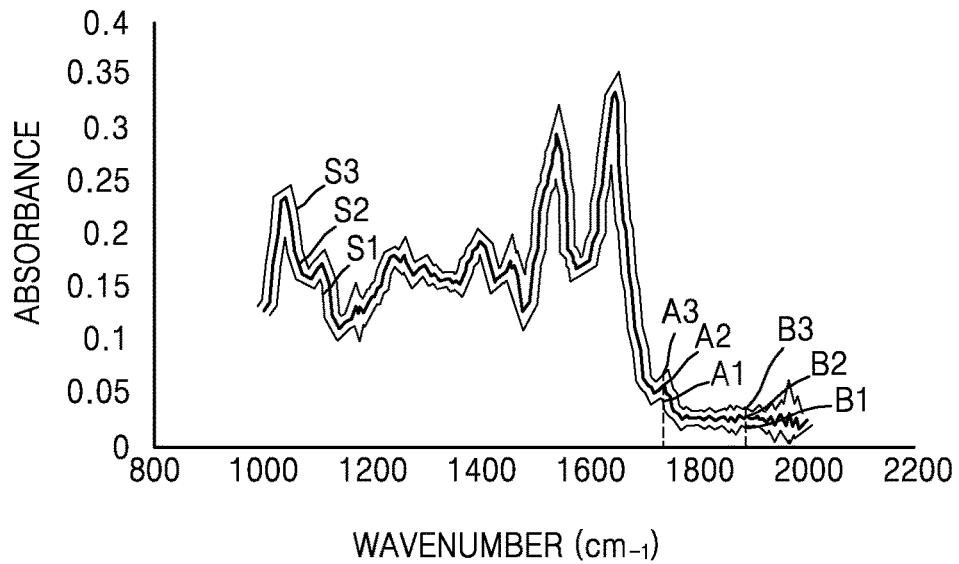
FIG. 9 is a graph for describing an operation of normalizing raw data in a non-invasive liver function testing apparatus according to an exemplary embodiment o.

When calculating a correlation between raw data of the target material and the liver function-related information, the raw data of the target material may be normalized. FIG. 9 illustrates an absorption spectrum based on several-time measurement of one object. An absorption spectrum may be differently measured due to several factors, such as a pressing force of a user and a change of a measured position, in each measurement. A measurement value may be normalized for decreasing a deviation of spectrums. For example, a first spectrum S1, a second spectrum S2, and a third spectrum S3 may be obtained, and absorbance A1, A2, and A3 corresponding to an absorption wavenumber A of a target material may be acquired. Absorbance may be normalized by expressing A1, A2, and A3 as a ratio to absorbance B1, B2, and B3 corresponding to a reference wavenumber B. The reference wavenumber B may be selected as one of wavenumbers which are not defined as an absorption wavenumber of another material in an absorption spectrum. Absorbance of each of spectrums shown in FIGS. 8A to 8G may be normalized.

Figure 10:
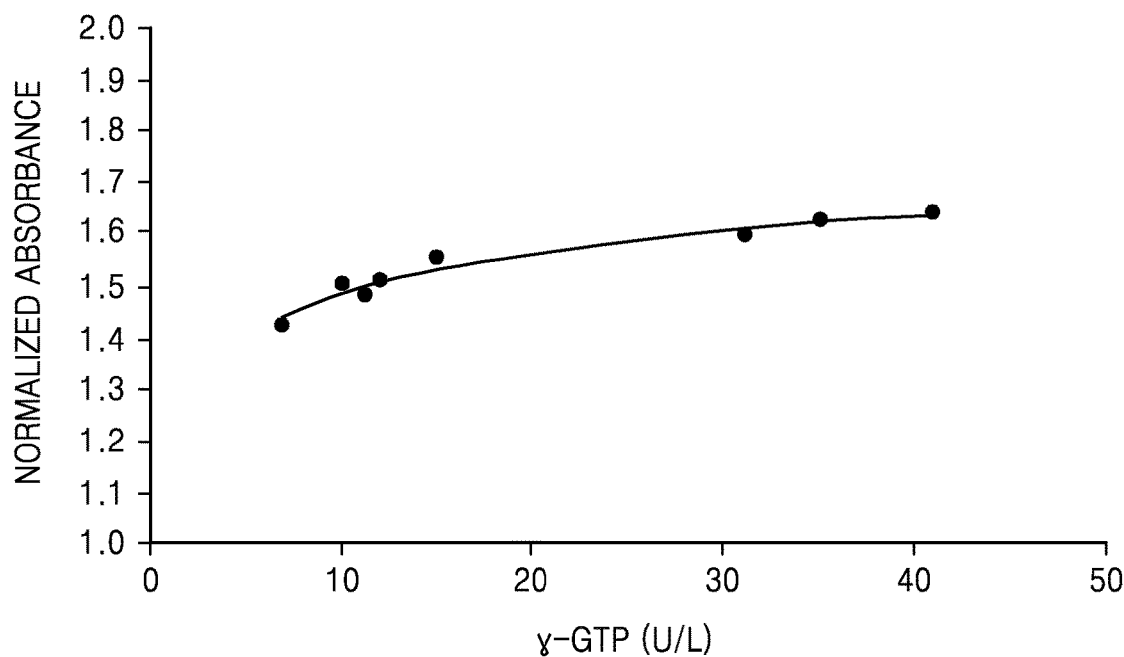
FIG. 10 illustrates an exemplary example of a correlation of raw data and liver function-related information which are used in an exemplary embodiment.

FIG. 10 shows, as a graph, a correlation between a normalized absorbance obtained from a plurality of objects and liver function-related information (a γ-GTP value) measured from blood of the plurality of objects. A correlation between raw data of a target material and liver function-related information may be drawn as a formula from the graph. For example, when an x axis of the graph indicates the γ-GTP value, and a y axis of the graph indicates a normalized absorbance, a relational formula "y=0.1103 ln(x)+1.2304" may be drawn. However, the relational formula is only an example of a correlation between a target material and the liver function-related information, and is not limited thereto. Also, an operation of obtaining a correlation between the target material and the liver function-related information may be performed by the data processor, or may be performed by a separate algorithm.

As described above, in an exemplary embodiment, liver function-related information may be drawn from raw data of a target material which is acquired by a non-invasive method using light.

Figure 11:
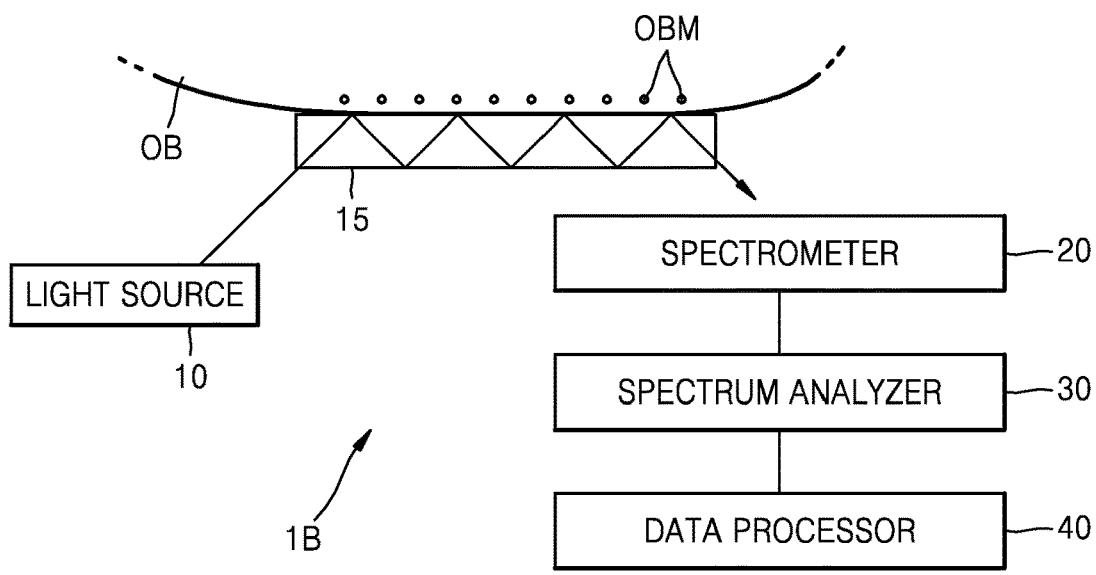
FIG. 11 illustrates an example in which the non-invasive liver function testing apparatus of FIG. 5 further includes an attenuated total reflectance prism.

A non-invasive liver function testing apparatus 1B of FIG. 11 may include a light source 10 that irradiates light L onto an object OB, a spectrometer 20 that divides light reflected from the object OB to acquire a spectrum, a spectrum analyzer 30 that extracts raw data, which is associated with at least one target material OBM constituting the object OB, from the spectrum, and a data processor 40 that draws liver function-related information, including a correlation with the at least one target material OBM, from the raw data. Also, an attenuated total reflectance prism 15 may be further provided between the light source 10 and the object OB. The light source 10, the spectrometer 20, the spectrum 30, and the data processor 40 are as described above with respect to FIG. 5, and thus, their detailed descriptions will not be repeated here.

The attenuated total reflectance prism 15 may be disposed in contact with the object OB. The attenuated total reflectance prism 15 broadens a reaction area with the object OB through total internal reflectance, and thus amplifies a spectrum signal detected by the spectrometer 20. Therefore, a target material of the object OB is more precisely detected by the attenuated total reflectance prism 15. The attenuated total reflectance prism 15 may be formed of a material having a higher refractive index than that of the object OB. The attenuated total reflectance prism 15 may closely contact the object OB. For example, the attenuated total reflectance prism 15 may further include at least one contact sensor, which detects whether the attenuated total reflectance prism 15 uniformly contacts an entire surface. A spectrum signal is more accurately obtained by reflecting a result of the detection.

Figure 12:
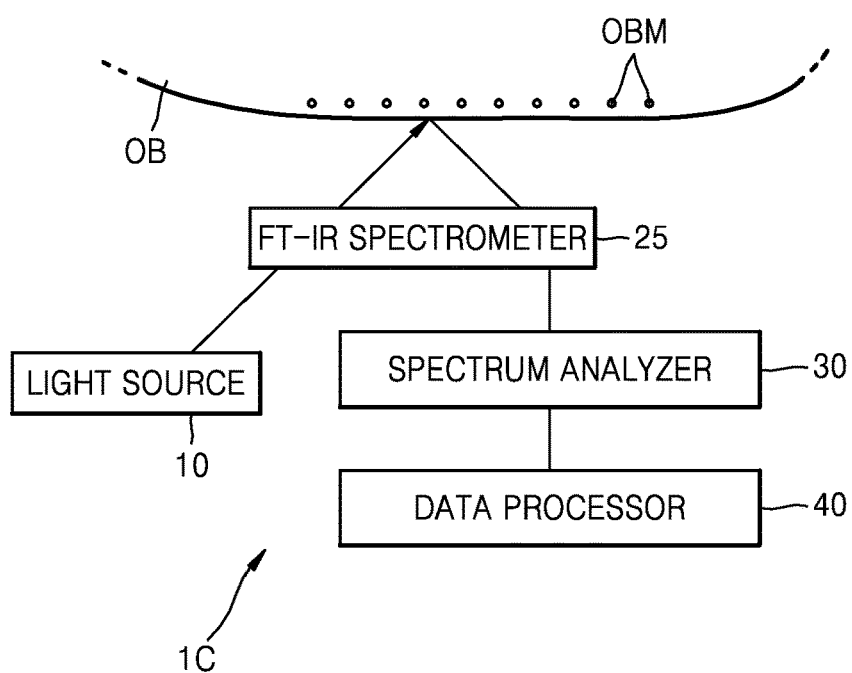
FIG. 12 illustrates an exemplary embodiment using a Fourier transform-infrared (FT-IR) spectrometer.

A non-invasive liver function testing apparatus 1C of FIG. 12 may include a Fourier transform-infrared (FT-IR) spectrometer 25. Comparing FIG. 12 with FIG. 5, a spectrometer is replaced by the FT-IR spectrometer 25, and the other elements may be used as-is. The FT-IR spectrometer 25 may perform Fourier transformation on an interference pattern by using an interferometer to obtain an absorption spectrum based on each wavelength from a time region to a vibration number region. The FT-IR spectrometer 25 simultaneously transmits light of a whole wavelength region through an object, and thus, time is saved. Also, infrared light having sufficient energy is irradiated, and high-sensitivity analysis is performed.

Although not shown, the non-invasive liver function testing apparatus 1C may further include an attenuated total reflectance prism (see 15 of FIG. 11) which is provided between the FT-IR spectrometer 25 and an object OB.

Figure 13:
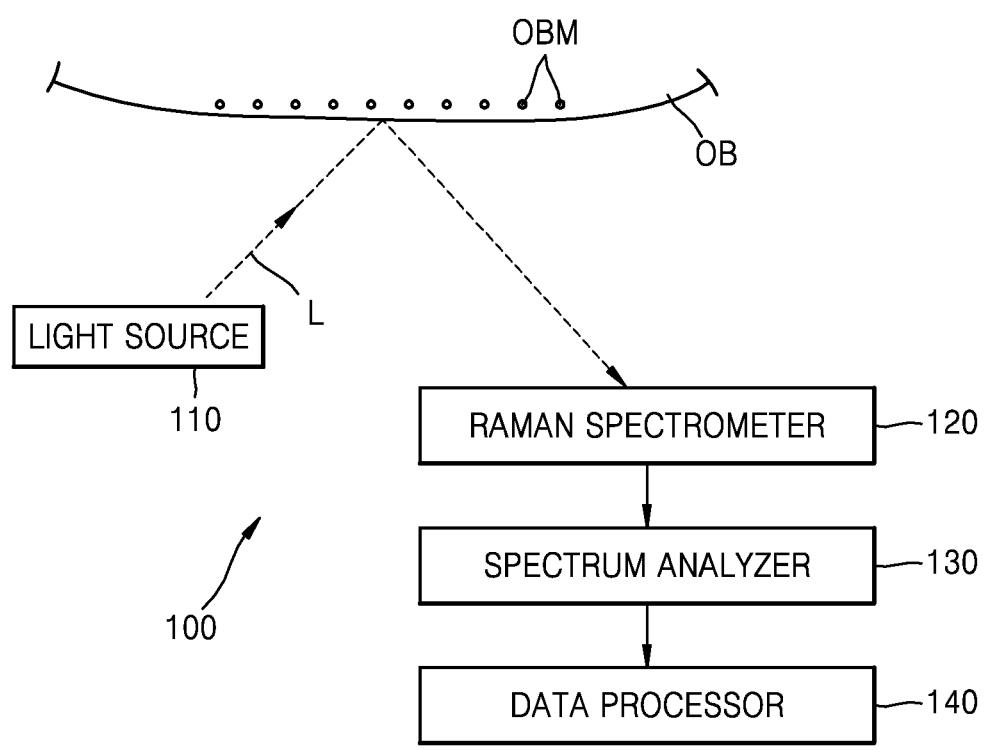
FIG. 13 illustrates another exemplary embodiment using an Raman spectrometer.

A non-invasive liver function testing apparatus 100 of FIG. 13 may include a light source 110 that irradiates light L onto an object OB, a Raman spectrometer 120 that divides light scattered from the object OB to acquire a spectrum, a spectrum analyzer 130 that extracts raw data, which is associated with at least one target material OBM constituting the object OB, from the spectrum, and a data processor 140 that draws liver function-related information, including information about a correlation with the at least one target material OBM, from the raw data.

The light source 10 may include, for example, a laser as a short-wavelength light source. However, the light source 10 is not limited thereto, and may be variously selected depending on a characteristic based on an interaction between light and the object OB.

The Raman spectrometer 110 may analyze light scattered from a target material of the object OB to detect molecular information about the target material. The spectrum analyzer 130 may extract raw data of a light characteristic (light intensity) corresponding to the target material from the spectrum. The data processor 140 may draw liver function-related information from the raw data. A correlation between the raw data and the liver function-related information has been described above, and thus, its detailed description will not be repeated here.

Although not shown, the non-invasive liver function testing apparatus 100 may further include an attenuated total reflectance prism (see 15 of FIG. 11) which is provided between the Raman spectrometer 120 and the object OB.

Figure 14:
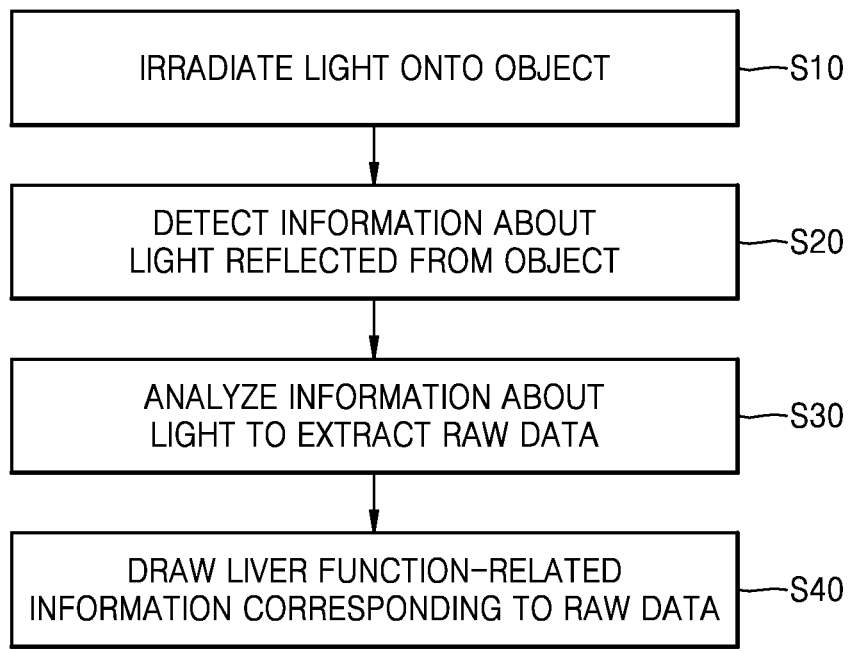
FIG. 14 schematically illustrates a non-invasive liver function testing method according to an exemplary embodiment.

Next, a non-invasive liver function testing method according to an exemplary embodiment will be described in detail with reference to FIG. 14.

The non-invasive liver function testing method according to an exemplary embodiment may include an operation (S10) of irradiating light onto an object and an operation (S20) of detecting information about light reflected from the object. The information about the light reflected from the object may be acquired by various methods. In the operation of detecting the information about the light reflected from the object, a spectrometer may divide the light reflected from the object to generate a spectrum. This will be described below.

In operation S30, raw data associated with at least one target material constituting the object may be detected from information detected by the light detector. The raw data may include, for example, the light characteristic (for example, light intensity) of a certain wavelength (or a wavenumber) corresponding to the target material. The at least one target material may include, for example, at least one material selected from the group consisting of glutamate, (5-L-glutamyl)-peptide, amino acid, peptide, 5-L-glutamyl amino acid, aspartate, α-ketoglutarate, oxaloacetate, L-gluramate, pyruvate, and L-alanine. The at least one target material may include at least one functional group selected from the group consisting of a —COOH (carboxylic acid) functional group, a —C=O (carbonyl) functional group, and a —C—N functional group.

In operation S40, liver function-related information having a correlation with the at least one target material may be extracted from the raw data. The liver function-related information may be calculated by using a predetermined lookup table or a predetermined correlational formula between the at least one target material and the liver function-related information. The liver function-related information may include, for example, a concentration of at least one enzyme selected from the group consisting of γ-gamma glutamyl transpeptidase (GTP), aspartate transaminase (AST), and liver transminase (ALT).

Figure 15:
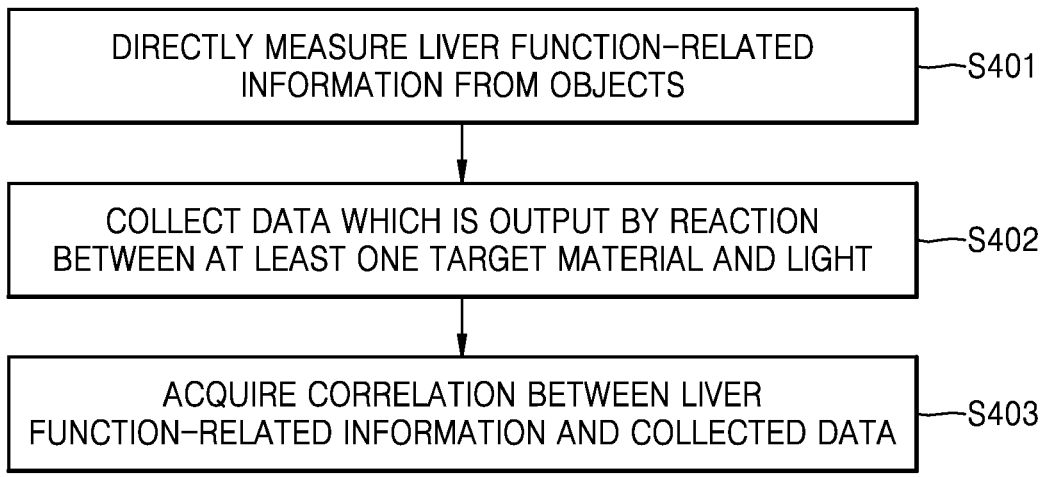
FIG. 15 illustrates a method of acquiring a correlation between liver function-related information and collected data in a non-invasive liver function testing method according to an exemplary embodiment.

Referring to FIG. 15, an operation of calculating the correlation may include an operation (S401) of directly measuring the liver function-related information from a plurality of objects, an operation (S402) of collecting data which is output by a reaction between the at least one target material and light, and an operation (S403) of acquiring a correlation between the liver function-related information and the data. The liver function-related information, for example, may be directly measured from blood by collecting blood from an object. Data of the at least one target material may be obtained by irradiating light onto the object. For example, the light may be transmitted to the epidermis or dermis of an object. However, the present embodiment is not limited thereto, and the light may be transmitted to a deeper position according to light intensity or force by which an object is pressed during testing. The data may be data of one target material. Alternatively, the data may be data of a plurality of target materials. A correlation between the measured liver function-related information and data corresponding thereto may be drawn. The correlation may be drawn by using various algorithms.

The correlation may include data of one target material and one piece of liver function-related information. Alternatively, the correlation may include complex data, which is obtained by combining data of a plurality of target materials, and one piece of liver function-related information. Alternatively, the correlation may include complex data, which is obtained by combining data of a plurality of target materials, and pieces of liver function-related information.

The correlation may be acquired as a relational formula or a lookup table, or may be acquired in various aspects.

Figure 16:
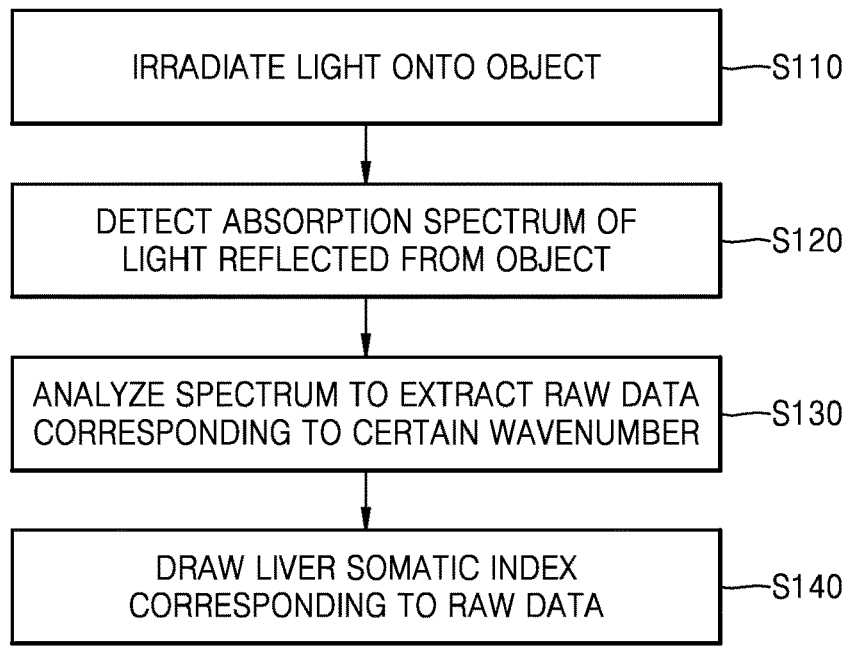
FIG. 16 illustrates a method of drawing a correlation between raw data of a target material and liver function-related information in a non-invasive liver function testing method according to an exemplary embodiment.

FIG. 16 illustrates an example of a method of analyzing light reflected from an object.

In operation S110, light is irradiated onto an object. The light may include infrared light. For example, the light may include mid-infrared light or near-infrared light. The mid-infrared light may have, for example, a wavelength having a range of 2.5 μm to 20 μm. The near-infrared light may have, for example, a wavelength having a range of 0.75 μm to 2.5 μm. However, a range of the mid-infrared light and a range of the near-infrared light may be changed depending on a light source or a target material which is used.

In operation S120, an absorption spectrum may be detected by dividing light reflected from the object. In operation S130, raw data corresponding to a certain wavenumber (or a wavelength) may be extracted by analyzing the absorption spectrum. The certain wavenumber (or the wavelength) may be a predetermined absorption wavenumber (or an absorption wavelength). The raw data may include light intensity (an absorbance) corresponding to the absorption wavenumber (or the absorption wavelength). Liver function-related information corresponding to the extracted raw data may be drawn from a correlation between raw data of at least one target material and liver function-related information.

Figure 17:
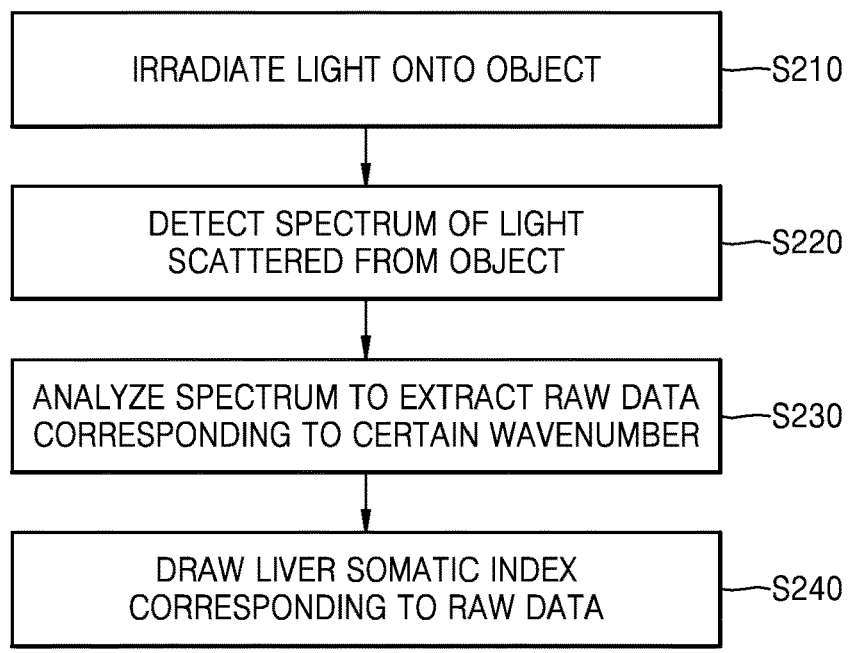
FIG. 17 illustrates a method using an absorption spectrum in a non-invasive liver function testing method according to another exemplary embodiment.

FIG. 17 illustrates another example of a method of analyzing light reflected from an object.

In operation S210, light is irradiated onto an object. The light may include a single color wavelength. In operation S220, a spectrum may be detected by dividing light scattered from the object. In the present embodiment, a scattering absorption spectrum may be obtained by using a Raman spectrometer. In operation S230, raw data corresponding to a certain wavenumber (or a wavelength) may be extracted by analyzing the spectrum. The certain wavenumber (or the wavelength) may be a predetermined wavenumber (or a predetermined wavelength) for each target material. The raw data may include light intensity corresponding to the certain wavenumber (or the wavelength). Liver function-related information corresponding to the extracted raw data may be drawn from a correlation between raw data of at least one target material and liver function-related information.

As described above, according to the one or more of the above exemplary embodiments, a liver function is simply tested by the non-invasive method without collecting blood from an object. By using the non-invasive method, a user conveniently uses the non-invasive liver function testing apparatus, and since the user may directly, frequently check a liver function, the non-invasive liver function testing apparatus helps health management. Also, the non-invasive liver function testing apparatus according to the embodiments of the present invention is applied to a mobile terminal, and a test result of a liver function which is directly tested by the user may be displayed in a mobile display. Also, the mobile terminal transmits the test result to a server of a hospital which the user uses, and the user's health is managed by the hospital server.

It should be understood that the exemplary embodiments described herein should be considered in a descriptive sense only and not for purposes of limitation. Descriptions of features or aspects within each embodiment should typically be considered as available for other similar features or aspects in other embodiments.

While one or more exemplary embodiments have been described with reference to the figures, it will be understood by those of ordinary skill in the art that various changes in form and details may be made therein without departing from the spirit and scope of the present invention as defined by the following claims.

What is claimed is:

1. A non-invasive liver function testing apparatus comprising:
   a data processor configured to store information about a correlation between first raw data, associated with at least one target material of a plurality of first objects and extracted by irradiating light onto the plurality of first objects, and liver function-related information obtained by collecting blood from the plurality of first objects;
   a light source configured to irradiate light onto a second object, the second object comprising the at least one target material;
   a light detector configured to detect information about light reflected from the second object; and
   a raw data extractor circuitry configured to extract second raw data, associated with the at least one target material of the second object, from the information detected by the light detector,
   wherein the data processor is further configured to determine liver function-related information corresponding to the second raw data, by using the information about the correlation.

2. The non-invasive liver function testing apparatus of claim 1, wherein the light detector comprises a spectrometer configured to divide the light reflected from the second object to generate a spectrum.

3. The non-invasive liver function testing apparatus of claim 2, wherein the raw data extractor circuitry comprises a spectrum analyzer configured to extract the second raw data, associated with the at least one target material of the second object, from the spectrum.

4. The non-invasive liver function testing apparatus of claim 2, wherein the spectrometer comprises an infrared spectrometer.

5. The non-invasive liver function testing apparatus of claim 4, wherein the spectrometer comprises a mid-infrared spectrometer or a near-infrared spectrometer.

6. The non-invasive liver function testing apparatus of claim 4, wherein the spectrometer comprises a Fourier transform-infrared (FT-IR) spectrometer.

7. The non-invasive liver function testing apparatus of claim 4, wherein the spectrometer further comprises an attenuated total reflectance prism.

8. The non-invasive liver function testing apparatus of claim 2, wherein the spectrometer comprises a Raman spectrometer.

9. The non-invasive liver function testing apparatus of claim 1, wherein the information about the correlation comprises a correlational formula or a lookup table.

10. The non-invasive liver function testing apparatus of claim 1, wherein the at least one target material comprises at least one functional group selected from the group consisting of a COOH group, a —C=O group, and a C—N group.

11. The non-invasive liver function testing apparatus of claim 1, wherein the liver function-related information corresponding to the second raw data comprises a concentration of at least one enzyme selected from the group consisting of aspartate transaminase (AST), liver transminase (ALT), and γ-gamma glutamyl transpeptidase (GTP).

12. The non-invasive liver function testing apparatus of claim 1, wherein the second raw data comprises data of light intensity with respect to a wavenumber corresponding to the at least one target material in a spectrum which is acquired by the light reflected from the second object.

13. The non-invasive liver function testing apparatus of claim 12, wherein the wavenumber comprises at least one selected from the group consisting of 1,740 cm$^{-1}$, 1,670 cm$^{-1}$ to 1,820 cm$^{-1}$, and 1,080 cm$^{-1}$ to 1,360 cm$^{-1}$.

14. The non-invasive liver function testing apparatus of claim 1, wherein,
the at least one target material comprises a material that is positioned at a first depth of the second object,
the liver function-related information corresponding to the second raw data comprises information of a material that is positioned at a second depth of the second object, and
the first depth is less than the second depth.

15. A non-invasive liver function testing method comprising:
storing information about a correlation between first raw data, associated with at least one target material of a plurality of first objects and extracted by irradiating light onto the plurality of first objects, and liver function-related information obtained by collecting blood from the plurality of first objects;
irradiating light onto a second object, the second object comprising the at least one target material;
detecting, by a light detector, information about light reflected from the second object;
extracting second raw data, associated with the at least one target material of the second object, from the information detected by the light detector; and
determining liver function-related information corresponding to the second raw data, by using the information about the correlation.

16. The non-invasive liver function testing method of claim 15, wherein the detecting of the information comprises dividing the light reflected from the second object by a spectrometer to generate a spectrum.

17. The non-invasive liver function testing method of claim 16, wherein the extracting of the second raw data comprises extracting the second raw data, associated with the at least one target material of the second object, from the spectrum.

18. The non-invasive liver function testing method of claim 16, wherein the detecting of the information is performed by an infrared spectrometer.

19. The non-invasive liver function testing method of claim 15, wherein the storing comprises:
collecting data which is output due to a reaction between the at least one target material of the plurality of first objects and the light irradiated onto the plurality of first objects; and
acquiring the correlation between the collected data and the liver function-related information obtained by collecting blood from the plurality of first objects and storing the correlation.

20. A non-invasive liver function testing apparatus comprising:
a data processor configured to store information about a correlation between light intensity with respect to a given wavenumber, obtained by irradiating light onto a plurality of first objects and detecting a spectrum acquired by light reflected from the plurality of first objects, and liver function-related information obtained by collecting blood from the plurality of first objects;
a light source configured to irradiate light onto a second object;
a light detector configured to detect information about light reflected from the second object; and
a spectrum analyzer configured to extract light intensity with respect to the given wavenumber of the second object, from the information detected by the light detector,
wherein the data processor is further configured to determine liver function-related information corresponding to the second object, based on the extracted light intensity and the correlation.

\* \* \* \* \*